United States Patent
Van Lare et al.

(10) Patent No.: US 9,815,773 B2
(45) Date of Patent: Nov. 14, 2017

(54) CRYSTALLINE PARTICLES OF GLUTAMIC ACID N,N-DIACETIC ACID

(71) Applicant: Akzo Nobel Chemicals International B.V., Amersfoort (NL)

(72) Inventors: Cornelis Elizabeth Johannus Van Lare, Wijchen (NL); Roy Gérard Doppen, Deventer (NL); Martin Heus, Arnhem (NL); Elwin Schomaker, Arnhem (NL); Paul Verwer, Nijmegen (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 28 days.

(21) Appl. No.: 14/649,273

(22) PCT Filed: Dec. 12, 2013

(86) PCT No.: PCT/EP2013/076371
§ 371 (c)(1),
(2) Date: Jun. 3, 2015

(87) PCT Pub. No.: WO2014/090942
PCT Pub. Date: Jun. 19, 2014

(65) Prior Publication Data
US 2015/0321995 A1 Nov. 12, 2015

Related U.S. Application Data

(60) Provisional application No. 61/751,348, filed on Jan. 11, 2013.

(30) Foreign Application Priority Data

Dec. 14, 2012 (EP) .................................... 12197176

(51) Int. Cl.
| | | |
|---|---|---|
| *B05D 1/02* | (2006.01) | |
| *C07C 227/42* | (2006.01) | |
| *C07C 229/24* | (2006.01) | |
| *C11D 3/33* | (2006.01) | |

(52) U.S. Cl.
CPC .............. *C07C 227/42* (2013.01); *B05D 1/02* (2013.01); *C07C 229/24* (2013.01); *C11D 3/33* (2013.01); *C07B 2200/13* (2013.01)

(58) Field of Classification Search
CPC ....... B05D 1/02; C07C 227/42; C07C 229/24; C11D 3/33; C07B 2200/13
See application file for complete search history.

(56) References Cited

U.S. PATENT DOCUMENTS

| | | | |
|---|---|---|---|
| 5,981,798 | A | 11/1999 | Schönherr et al. |
| 6,265,371 | B1 | 7/2001 | Hagino et al. |
| 2008/0194873 | A1 | 8/2008 | Oftring et al. |
| 2012/0046491 | A1 | 2/2012 | Mrzena et al. |
| 2012/0149936 | A1 | 6/2012 | Baranyai |
| 2012/0252708 | A1 | 10/2012 | Van Lare et al. |
| 2015/0353475 | A1 | 12/2015 | Doppen et al. |

FOREIGN PATENT DOCUMENTS

| | | | |
|---|---|---|---|
| DE | 4211713 A1 | 10/1993 | |
| EP | 0591934 | * | 4/1994 |
| EP | 0591934 A1 | 4/1994 | |
| EP | 0845456 A2 | 6/1998 | |
| EP | 0884381 | * | 12/1998 |
| EP | 0884381 | 12/1998 | |
| EP | 1004571 A1 | 5/2000 | |
| GB | 1439518 | 6/1976 | |
| JP | H07-242607 A | 9/1995 | |
| JP | H10-077253 A | 3/1998 | |
| JP | H11-043689 A | 2/1999 | |
| JP | H11-246497 A | 9/1999 | |
| JP | 2002-088037 A | 3/2002 | |
| JP | 2002-356464 A | 12/2002 | |
| JP | 2004/359700 A | 12/2004 | |
| WO | 2008/065109 A1 | 6/2008 | |
| WO | 2009/024519 A1 | 2/2009 | |
| WO | 2010/076291 A1 | 7/2010 | |
| WO | 2011/076769 A1 | 6/2011 | |
| WO | 2011/079940 A1 | 7/2011 | |
| WO | 2011/146582 A1 | 11/2011 | |
| WO | 2012/000915 A1 | 1/2012 | |
| WO | 2014/090943 A1 | 6/2014 | |

OTHER PUBLICATIONS

International Search Report and Written Opinion for PCT/2013/076371, dated Mar. 11, 2014.
European Search Report for 12197176.6 dated May 14, 2013.
Dissolvine GL Technical Brochure, Apr. 2010 (Apr. 2010), pp. 1-16, XP055058393.

* cited by examiner

*Primary Examiner* — Paul A Zucker
*Assistant Examiner* — Mark Luderer
(74) *Attorney, Agent, or Firm* — Sandra B. Weiss

(57) ABSTRACT

The invention relates to glutamic acid N,N-diacetic acid (GLDA) of the formula $GLDA\text{-}Y_mH_n$, wherein m is less than 0.5, n+m=4, Y is a monovalent cation that is not a proton, in the form of crystals, a process to make these crystals, and their uses, in particular in detergent compositions.

16 Claims, 3 Drawing Sheets

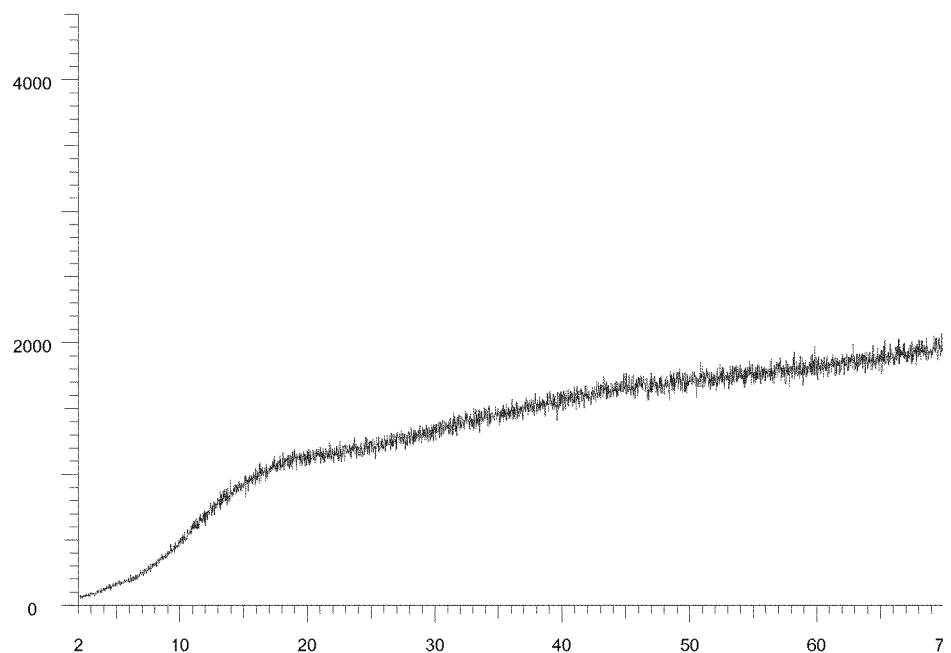
Figure 1 XRD of amorphous GLDA acid of Example 4

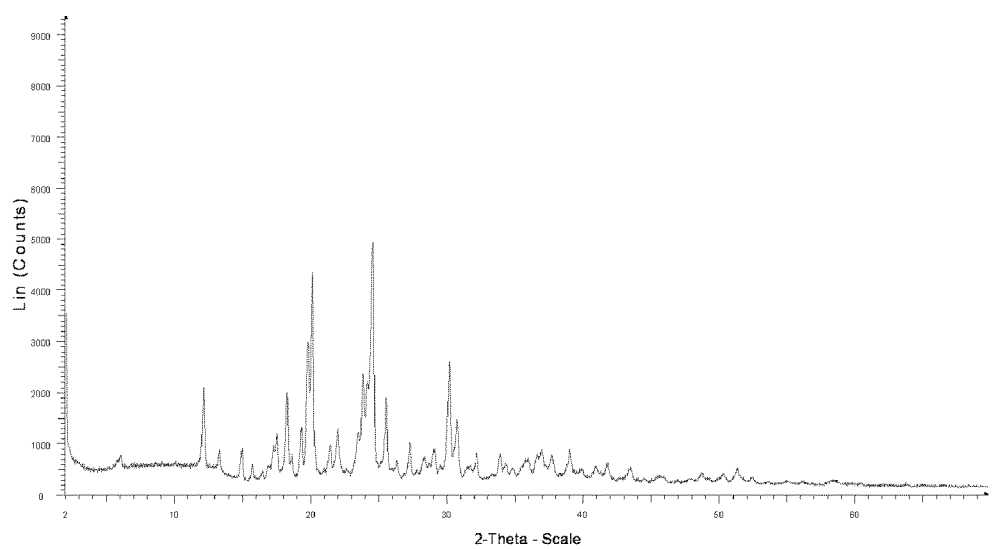
Figure 2 XRD diffractogram of crystals of GLDA-H$_4$ of Example 2

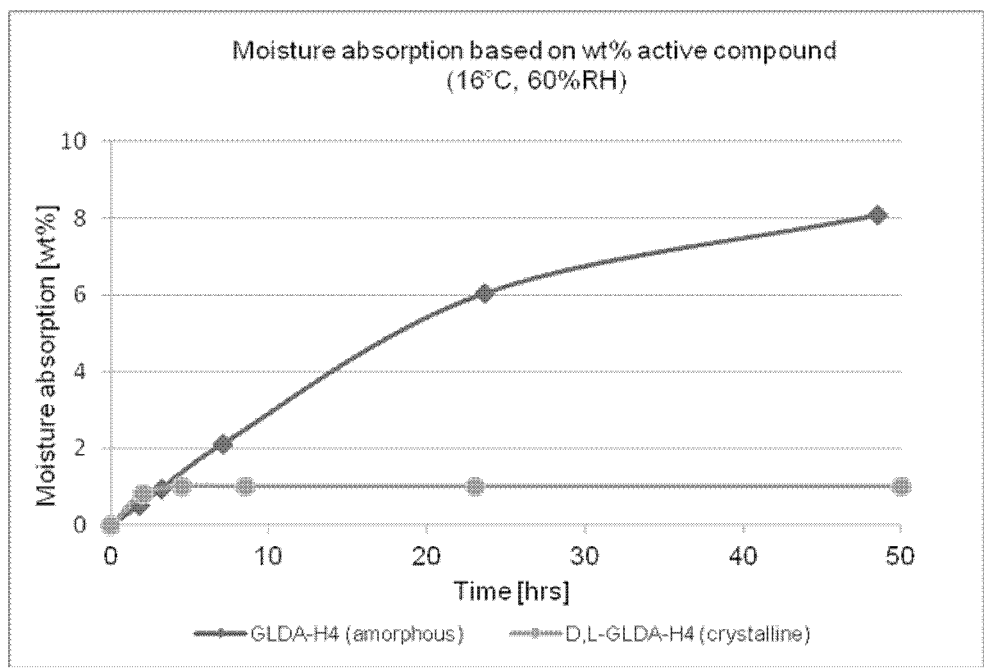
Figure 3: Moisture absorption of crystalline versus amorphous GLDA acid.

CRYSTALLINE PARTICLES OF GLUTAMIC ACID N,N-DIACETIC ACID

This application is a national stage filing under 35 U.S.C. §371 of PCT/EP2013/076371, filed Dec. 12, 2013, which claims priority to U.S. Provisional Patent Application No. 61/751,348 filed Jan. 11, 2013, and European Patent Application No. 12197176.6, filed Dec. 14, 2012, the contents of which are each incorporated herein by reference in their entireties.

The invention relates to crystalline particles of glutamic acid N,N-diacetic acid, a chelating agent of the formula COOH—CH(—CH$_2$—CH$_2$—COOH)—N—(CH$_2$—COOH)$_2$, abbreviated as GLDA or in the full acidic form GLDA-H$_4$, to processes to produce said particles, and to the use of such particles.

The detergent market is currently undergoing important changes. Due to ecological and regulatory reasons the use of phosphate in high concentrations in detergent formulations is to be banned altogether or must at least be greatly reduced. The formulators of detergent products have to find alternatives to replace the phosphate compounds, with the most promising replacements being biodegradable chelating agents such as GLDA. Such chelating agents are used in a concentration from 5% to 60%. Many detergent formulations contain co-builders, which are typically polymers or phosphonates and also phosphates, silicates, and zeolites. These co-builders are present in formulations in a concentration from 1% to 50%.

In powder or tablet detergent formulations, solid raw materials are required by the formulator. For example, in automatic dishwashing (ADW) applications the raw materials have to be in granule form to improve the tabletting and solids handling of the formulation. These granules typically have a size comprised between 100 and 3,000 microns. The usual form in which glutamic acid N,N-diacetic acid (GLDA) and its salts are available is a solution with an active content from 35% to 60%. After drying, the powder or granules, when obtained in the amorphous state, show extensive hygroscopic properties, which is unacceptable for the ADW formulators. Whether in powder or granule form, the amorphous chelating agent GLDA exhibits hygroscopic properties, rendering the material sticky and thus introducing storage, handling, and manufacturing problems. Flow properties of particles are critical in many ways. During manufacture of the particles themselves, they must flow smoothly relative to one another. Additionally, they must then be successfully transported to storage and transport containers. Finally, they must again be transported from storage and fed into a powder or tablet manufacturing facility. Flow problems arise due to several causes. In the case of amorphous GLDA and its salts poor flow will be caused by moisture pick-up, resulting in a wet sticky product that will form lumps.

GLDA will definitely move into the ADW market and likely into many other fields where a strong, green chelate is needed. The term "green" here denotes materials with a high renewable carbon content, a sustainable environmentally friendly production process, and a positive biodegradability assessment. While the state of the art builders used in detergent formulations, such as sodium tripolyphosphate (STPP) and nitrilo triacetic acid (NTA), are isolatable as dry particles, the hygroscopic, dusty, and sticky properties of solid amorphous GLDA are disadvantageous and make co-granulation and/or coating necessary, so it would be highly desirable to improve the non-hygroscopic properties of GLDA. WO2011/076769 for example discloses coating particles of amorphous GLDA-H$_4$ or one of its salts to improve the hygroscopic properties.

US20120046491 discloses the preparation of a powder comprising one or more derivatives of glutamine-N,N-diacetic acid or glycine-N,N-diacetic acid with a degree of crystallinity of ≥30%, the process comprising concentrating an aqueous solution to obtain a crystal slurry, wherein one concentration range is from 20% to 60% by weight (starting material), based on the total weight of the crystal slurry, and ripening the crystal slurry in a paste bunker and then in a thin-film contact dryer, wherein the residence time in the paste bunker (seeds: fine powder up to 50% of total weight) and in the thin-film contact dryer is in total ≥15 min and the concentration occurs in an evaporator with rotating internals which are arranged at a distance relative to an inside wall of the evaporator of ≤1% of a diameter of the evaporator (high shear rate in the liquid film on the inside wall). Temperature ranges for the first process step are between 50° C.-140° C. and preferably between 80° C.-110° C., and pressure ranges are between 0.1 and 4 bar, preferably between 0.8 and 1.2 bar. Ripening is carried out for at least 15 minutes and up to 3 hours and thin-film treatment is carried out for between 0.5 minutes and 20 minutes from 60° C. up to 140° C. A powder is obtained which predominantly has the crystal modification of the monohydrate or the dihydrate of MGDA (methylglycine diacetic acid). The complicated process appears to be specifically designed for MGDA and is not reproducible for GLDA or its salts, in particular since the temperature ranges of the process are too high for the crystallization of GLDA.

US20120149936 discloses a process for preparing crystalline solids of glycine-N,N-diacetic acid derivatives of sufficiently low hygroscopicity by introducing one crystalline compound as a seed, and a spray granulation is carried out, which may be followed by a heat treatment step to increase the crystallinity. Only glycine-N,N-diacetic acid derivatives are mentioned in the document and, again, the temperatures are too high for the crystallization of GLDA.

EP 845 456 discloses the preparation of a crystalline solid of a glycine N—N-diacetic acid derivative. In the Examples a concentrated solution of the trisodium salt of MGDA (methylglycine N,N-diacetic acid) is crystallized using seeds as crystallization initiator. However, this process is not reproducible for GLDA and its salts, as the same will not crystallize under the cited conditions; the GLDA at high concentrations becomes extremely viscous and crystallization will not occur.

DE 42 11 713 discloses a process to prepare the chelating agents GLDA and ASDA (aspartic acid N,N-diacetic acid). Though it is suggested in general that the materials could be isolated by several methods, one of which is crystallization, all the examples deal with depositing ASDA in the amorphous form.

EP 1004571 discloses a process to prepare an aqueous solution of GLDA and the crystallization of the ammonium ferric salt thereof. This patent makes use of the completely changed properties of a metal chelate in comparison to a chelating agent without a metal ion being chelated.

JP2002356464 discloses a process to prepare highly pure (salt-free) solutions of chelating agents and suggests crystallizing them in the acidic form and subsequently dissolving them in an aqueous solution. However, the preparation of a highly pure GLDA acid solution is done by converting a solution of GLDA salt to an acidic form using an ion exchange resin and then adjusting the pH to the right value by the addition of an amine. No solid materials are disclosed or exemplified.

A few documents seem to disclose the preparation of crystals of GLDA, EP-A-0 591 934 in Synthesis Example 2, and EP-A-0 884 381 in Synthesis Example 1. A Japanese patent application, JP 11 043689, discloses the same synthesis for GLDA as EP-A-0 884 381. However in the Example of EP-A-0 591 934 the pH is higher than it should be for preparing GLDA acid crystals, and if this document leads to anything, it will be a GLDA-Na$_m$ solid material wherein m is higher than 0.5. In addition, the procedures from EP-A-0 884 381 and EP-A-0 591 934 when reworked were not found to give any GLDA crystals.

GB 1 439 518 A refers to alleged literature giving a process for making GLDA related molecules that when crystallized are very hygroscopic. First of all, the literature to which reference is made is unidentified and, besides, we have now established that crystals of GLDA are not very hygroscopic, so this reference to earlier literature must be inaccurate to some extent.

Several documents disclose the crystallization of chelating agents (also often referred to as aminopolycarboxylic acids). Thus JP 2002088037, JP 07242607, JP 2004359700 mention or disclose the crystallization of a number of amino acid diacetic acids. None of these documents relates to GLDA, nor to crystallization of GLDA.

JP 1998/077253A discloses the preparation of a solid aminodicarboxylic acid N,N-diacetic acid by crystallization in a solution of a pH of about 2 and addition of methanol. Where this process is repeated for GLDA, the document speaks of solid GLDA instead of crystalline GLDA and no disclosure or evidence is shown (e.g. in the form of XRD or DSC results) that the material produced is crystalline.

The disadvantage of the prior art is that the processes disclosed for MGDA, apart from being complex, do not work for GLDA or produce solid yet amorphous material. The prior art does not disclose an enabled process to produce crystalline GLDA.

As described above, solid amorphous GLDA (available as commercial product) has the disadvantage of being hygroscopic.

Therefore, less hygroscopic GLDA chelating agents are needed which show improved storage, handling, transport, and flowing properties.

Quite surprisingly, it has been found possible to isolate particles of GLDA in the form of crystals. This holds even more since it has been found that making a crystalline particle of GLDA is by no means a straightforward process when applying commonly known techniques such as anti-solvent crystallization and salting-out processes.

Accordingly, the present invention provides particles of glutamic acid N,N-diacetic acid (GLDA) of the formula GLDA-Y$_m$H$_n$, wherein m on average is less than 0.5 and n+m=4, Y is a monovalent cation that is not a proton, in the form of crystals. Preferably, m is (about) 0 and the cation Y is not present or only present in trace amounts. These crystalline particles of GLDA show a reduced hygroscopic behaviour compared to the equivalent amorphous particles and are biodegradable.

According to this invention, a solid compound is crystalline when it has a three-dimensional periodic structure (crystal). A three-dimensional periodic structure is different from an amorphous structure in that it shows interference in monochromatic X-ray diffraction which fulfills the Bragg equation (2 d sin $\Theta$=n$\lambda$), whereas amorphous materials produce a broad background signal (FIG. 1). The crystalline particle of the present invention further exhibits reduced hygroscopicity compared to amorphous particles of GLDA.

Description of the Figures

FIG. 1 is an illustration of an X-ray diffraction pattern obtained from the amorphous GLDA-H4 of Example 4.

FIG. 2 is an illustration of the X-ray diffraction pattern obtained from the GLDA-H4 crystals of Example 2.

FIG. 3 is a comparison of the moisture uptake of amorphous GLDA-H4 and the crystalline GLDA-H4 as a function of time, as determined in Example 4.

In a further embodiment, the biodegradable crystalline GLDA of the invention comprises L-GLDA-Y$_m$H$_n$ to D-GLDA-Y$_m$H$_n$ in a range of from 100:0 to 50:50 (L:D). In a preferred embodiment L-GLDA-Y$_m$H$_n$ to D-GLDA-Y$_m$H$_n$ is between 100:0 and 90:10 (i.e. is (substantially) optically pure L-GLDA-Y$_m$H$_n$). In another preferred embodiment L-GLDA-Y$_m$H$_n$ to D-GLDA-Y$_m$H$_n$ is (about) 50 to 50, i.e. the product is a racemic mixture of (more or less) equal quantities of the two enantiomers L-GLDA-Y$_m$H$_n$ and D-GLDA-Y$_m$H$_n$, which racemic mixture is readily biodegradable as optically pure product. Each enantiomer rotates the plane of polarization of plane-polarized light through a characteristic angle, but because the rotatory effect of each component exactly cancels that of the other, the 50:50 mixture is optically inactive.

The crystalline particles of the invention in one embodiment have a particle size of 20 to 3,000 microns ($\mu$m), preferably of 500 to 2,000 microns, most preferably between 50 and 300 microns.

The disadvantage of particles which are too small is that the obtained product is e.g. dusty, which reduces manageability and also easier caking is observed. The disadvantage of particles which are too large is e.g. that these particles take longer to dissolve, which makes them less suitable for detergent, such as ADW, applications.

In addition, the present invention provides a process to prepare the particles of GLDA-Y$_m$H$_n$ wherein the GLDA-Y$_m$H$_n$ is crystalline, comprising in a first step providing an aqueous solution containing GLDA-Y$_m$H$_n$ or a precursor thereof, in a second step ensuring that the pH of the aqueous solution is below 1.8, and in a third step allowing the aqueous solution to crystallize, wherein in the aqueous solution that is allowed to crystallize the amount of GLDA-Y$_m$H$_n$ is at least 15 wt % on total solution weight, m is less than 0.5, n+m=4, and Y is a monovalent cation that is not a proton.

Preferably, the amount of GLDA-Y$_m$H$_n$ is at least 20 wt % on total solution.

In another preferred embodiment, at least 75 wt % of the total organic compounds in the aqueous solution that is allowed to crystallize is GLDA-Y$_m$H$_n$. Organic compounds are defined as hydrocarbon based compounds (compounds that contain at least one covalent hydrogen-carbon bond) and include compounds that can be considered impurities formed during the preparation of GLDA-Y$_m$H$_n$ such as formaldehyde, nitrilotriacetic acid, glutamic acid, glycolic acid, formic acid, or glutamic acid N-monoacetic acid (=GLMA, which can be both linear and cyclic). More preferably, at least 85 wt % on the total weight of organic compounds in the solution is GLDA-Y$_m$H$_n$, most preferably at least 90 wt %.

In yet another preferred embodiment, the weight amount of GLDA-Y$_m$H$_n$ on total inorganic compounds in the solution, i.e. the weight ratio GLDA-Y$_m$H$_n$:inorganic compounds, in the solution allowed to crystallize is higher than 1:1, more preferably higher than 2:1, and most preferably higher than 3:1, wherein inorganic compounds are compounds that are not organic compounds as defined above and not water. Inorganic salts are the most important examples of inorganic compounds. It was found that salting out acidic GLDA crystals is very complex and increasing the salt load merely has an inhibiting effect on the crystallization of the organic GLDA-$Y_mH_n$ compound.

It was found that if the process is performed at a pH lower than 1.8, preferably pH between 1.0 and 1.7, crystallization of GLDA in the acidic form is very well possible. It was additionally found that GLDA crystals are significantly less hygroscopic when compared to solid amorphous GLDA.

The aqueous solution of the first step may be an aqueous solution of GLDA and/or of one of its precursors, in particular, an aqueous solution of a salt of GLDA, such as GLDA-$Na_4$.

The second step in embodiments where the starting solution has a different pH involves an acidification, wherein the pH is adjusted to be below 1.8, preferably in the range of between 1.0 and 1.7.

In the second step of the process the pH of lower than 1.8 may be ensured by acidification using an electrolytical, e.g. Bipolar Membranes (BPM), acidification process, such as described in e.g. EP-A-1004571 or WO 2008/065109, by using ion exchangers and/or by adding an inorganic acid to the aqueous solution until the aqueous solution has a pH of lower than 1.8. If ion exchangers are used, the aqueous solution may further be sieved in order to remove any ion exchange resin residues.

The pH in the second step of the process according to this invention is defined as the pH of the solution when measured for a 5 wt % aqueous solution, at a temperature of 30° C. The pH of GLDA is preferably approx. 1.4 under these conditions. Of course, this does not imply that the solution of the second step should contain 5 wt % of GLDA; as explained below, it is preferably more concentrated.

The second step may further comprise an optional concentrating step.

The concentrating step may be carried out until the critical concentration of the aqueous solution, the supersaturation, is reached. The concentrating step of the process may be carried out until the aqueous solution has a concentration of equal to or more than 15 wt % up to or equal to 80 wt %, more preferably more than 20 wt % up to or equal to 80 wt % of GLDA-$Y_mH_n$, based on the weight of the aqueous solution. When the more concentrated solutions are so viscous that an efficient crystallization becomes more difficult, the skilled person will know that reducing the viscosity thereof, for example by heating the solution, may be desirable.

In a further embodiment, the aqueous solution may be concentrated in the concentrating step by way of evaporation, optionally at an elevated temperature.

The second step of the process optionally comprises a racemization step. The racemization step in a preferred embodiment takes the form of a temperature treatment step. The temperature treatment step according to this invention is a temperature and time-dependent treatment which may comprise allowing the solution to stand for an extended period of time (months) at room temperature. The temperature treatment step preferably comprises heating the aqueous solution to between 90° C. and 140° C., preferably to between 98° C. and 137° C., for a shorter period of time (hours). In some embodiments, the temperature treatment step may involve an increased pressure.

If optically pure products (100:0 L:D-GLDA) are desired, care has to be taken to ensure that no racemization occurs during the second step. In particular, the temperature during the process should be kept below 35° C., preferably 30° C.

In the third step of the process wherein the solution is allowed to crystallize in some embodiments the solution is allowed to stand for an extended period of time, a cooling and/or, a seeding step are performed.

When a cooling step is performed in the third step, cooling may be batch controlled-cooling, e.g. using predetermined temperature profiles.

When seeding is done in the third step to allow the product to crystallize, the seeding may for example comprise adding dust and/or glass particles, crystals of the respective crystalline salt. Seeding may be carried out by way of macro- or micro-seeding, temperature shocks, vibration and/or providing a suitable surface for adhesion. Seeding may be carried out at elevated temperatures and/or stepwise.

The third step of the process may further be carried out by spraying the aqueous solution of the third step on seeding crystals.

The third step of the process is preferably performed at a temperature of equal to or below 35° C., preferably 30° C. Preferably, during the crystallization process the solution of GLDA is cooled to a temperature of equal to or below 25° C. In more preferred embodiments the temperature is at least 0° C.

In a further embodiment, the process according to this invention may further comprise an optional separation step, wherein the crystalline product of the third step is separated from the mother liquor (that part of the aqueous solution which is left after crystallization).

The process according to this invention may optionally comprise a drying step in which the crystalline particle of GLDA is dried. Drying may be conducted at elevated temperatures and/or under reduced pressure, preferably vacuum.

The process according to this invention can be carried out as a continuous process, e.g. by using resulting products as seeds in the third step. Crystallization may also be induced repeatedly in the separated mother liquor.

In a further embodiment, it is possible to add carbonates/bicarbonates and/or silicates to the resulting product of the third step, so that the pH of an aqueous solution of the resulting product is above 6. In one embodiment the crystals are mixed, co-granulated or coated with a sufficient quantity of carbonates and/or silicates. Most preferably, the carbonates and/or silicates are sodium based.

The invention also provides the use of the crystalline particles of GLDA-$Y_mH_n$ in detergents (in which the GLDA-$Y_mH_n$ can be mixed with carbonate/bicarbonate and/or silicate to increase the pH to neutral or higher as often required in cleaning), agriculture, in oil field applications, feedstock applications, pharmaceutical applications, in water treatment, and in other applications that require or profit from the benefits provided by this invention, i.e. the sequestration of metal ions which can otherwise lead to precipitation, low hygroscopicity, inhibition or dissolution of scale growth and pH. One preferred embodiment of this invention is the use of the particles in automatic dish washing formulations. Another preferred embodiment of this invention is the use of the particles in oil well completion and production operations.

The crystalline particles of GLDA-$Y_mH_n$ are an excellent feedstock to produce metal-GLDA products, as their sufficiently low pH after dissolution allows reaction with metal oxides/metal hydroxides at sufficient speed and under mild conditions, so avoiding the need for the more expensive metal salts while at the same time avoiding the disadvantage of introducing (a high amount of) a sodium or potassium salt into the aqueous metal-GLDA solution.

The invention additionally relates to detergent compositions containing crystalline particles of GLDA-$Y_mH_n$ and further comprising at least one component selected from the group of cleaning additives, antiscaling additives, builders, protective colloids, chelating agents, surfactants, corrosion inhibitors, and organic or inorganic acids.

The invention additionally relates to pharmaceutical preparations containing crystalline particles of GLDA-$Y_mH_n$, and further comprising a pharmaceutically acceptable carrier, preferably lactose derivatives and/or cellulose derivatives.

EXAMPLES

The materials used are:
Dissolvine GL-47-S (a 47 wt % solution of L-GLDA-$Na_4$ tetrasodium salt in water), ex Akzo Nobel Functional Chemicals LLC, Chicago Ill., USA.
XRD Method and Equipment Used for Analysis The diffractograms of crystalline GLDA according to this invention were recorded using a Bruker-AXS D8 reflection-diffractometer using Ni filtered Cu-$K_\alpha$ radiation. Generator settings are 40 kV, 40 mA. A graphite monochromator was used with divergence and anti-scatter slit V20 (variable 20 mm), detector slit 0.6 mm. The measuring range was 2Θ=2.0-70.0°, step size 0.02°, time per step 6.5 seconds.

The Topas software package from Bruker was used for the diffractograms.

NMR in this document means $^1$H NMR.
CZE stands for Capillary Zone Electrophorese.

Example 1 Acidification of GLDA Solutions

To produce the GLDA-$H_4$ solution, the pH of a GLDA-$Na_4$ Dissolvine GL-47-S solution was lowered to about 1.2, using a Bi-Polar Membranes (BPM) process. In the BPM process, a bipolar membrane electrodialysis stack was used as described in WO 2008/065109. Such a unit consists of bipolar membranes and a cation exchange membrane. The sodium cations are removed through the cationic exchange membrane, while the hydrogen is added into the product stream via an electrochemical reaction. That way the solution is gradually acidified without having residual sodium cations present. This means that a "salt-free" acidification has occurred.

The experimental set-up consisted of three vessels to recycle fluids through the BPM unit. The temperature was controlled by applying heating/cooling to the jacketed reactors. The acid reactor was a 1 l stirred glass reactor and the base and electrolyte loop both used 1.5 l glass reactors without stirring. Nitrogen was passed through the electrolyte solution via a gas sparger in order to dilute the hydrogen gas produced at the cathode to far below the explosion limit.

The reactor was charged with a ca 40 wt % GLDA-$Na_4$ solution and the recirculation of the reactor content over the BPM stack was started. Once the GLDA-solution was heated to 40° C., an electric current was applied. The voltage (V) over the stack was limited to 25V and the electric current (I) was controlled manually to a maximum of 15 A. When the desired pH was reached, the current to the BPM was minimized and both the reactor and BPM contents were collected. The acidified GLDA solution was established to be a 44 wt % L-GLDA solution with a pH of about 1.2 as is.

Example 2 Preparation of D,L-GLDA-$H_4$ 870 g of 44 wt % L-GLDA-$H_4$ aqueous solution prepared in accordance with Example 1, which means a saturated solution, were heated to 80° C. in a glass container until supersaturation was reached. The aqueous solution was allowed to stand in a well-closed container for 63 days at 80° C. in an oven, allowing the concentrated aqueous solution to crystallize.

The precipitate in the mother liquor was ground and the obtained slurry was filtered applying a G3 glass filter.

The wet cake was subsequently washed twice with a small amount of ice water and dried under vacuum at ambient temperature. After drying 152.3 g GLDA-$H_4$-crystals were obtained (first crop).

The warm mother liquor was allowed to cool to ambient temperature within 20 minutes.

During cooling the mother liquor showed fast crystallization.

Evaluation of the slurry applying an optical microscope displayed hexagonal crystals and agglomerates.

The obtained slurry was filtered applying a G3 glass filter and the remaining wet cake was washed twice with a small amount of ice water.

The wet cake was dried under vacuum at ambient temperature, yielding a second crop of 102.7 g dry crystals at assay Fe-TSV=92.7%. Optical rotation=0°.

An XRD was taken of crystals from the second crop.
FIG. 2 shows an XRD of the obtained crystals, which shows interference fulfilling the Bragg equation.

Example 3 Preparation of L-GLDA-$H_4$ 3 l of Dissolvine GL-47-S aqueous solution were acidified to a pH of 1.2 as is, using BPM.

The resulting 44 wt % L-GLDA-$H_4$ aqueous solution was concentrated to a 50 wt % L-GLDA-$H_4$ aqueous solution using a rotavapor, water bath temperature 30° C., and reduced pressure (20 mbar).

2,500 g of the resulting solution were pre-charged into a 3 l jacketed glass reactor provided with an anchor stirrer.

The aqueous solution was maintained at ambient temperature, the clear solution was seeded with 5.3 g L-GLDA-$H_4$ crystals with stirring and stirred overnight.

The crystal slurry was centrifuged in a horizontal Rousselet drum centrifuge to separate the mother liquor from the crystalline product.

After separation, 1,992 g of mother liquor with a concentration of 42.7% (established by way of Fe-TSV, Iron Total Sequestering Value) and 800.0 g of wet cake were obtained. The wet cake was dried under vacuum at 45° C. yielding 612 g of dry material established to be L-GLDA-$H_4$ crystals by XRD.

Example 4 Hygroscopicity Tests on GLDA Acid 10.016 g of the D,L-GLDA-$H_4$ crystals prepared in Example 2 were compared to amorphous GLDA-$H_4$ with regard to their hygroscopicity.

Dissolvine GL-47-S was acidified to a pH of 1.2 in accordance with Example 1.

The aqueous GLDA solution was spray-dried applying a NIRO A/S MOBILE MINOR™ spray dryer at an inlet temperature of 220° C., an outlet temperature of 115° C., and a spray pressure nozzle (gap=1 mm) of 1 bar.

The hygroscopic properties of the obtained amorphous powder were compared to the crystals using a moisture absorption test.

10.016 g GLDA-$H_4$ crystals and 10.000 g spray-dried (amorphous) GLDA-$H_4$ were weighed in. Both solids were stored at 16° C. and 60% Relative Humidity.

After 48.5 hrs the weight was found to be 10.116 g for the crystalline GLDA-$H_4$ and 10.807 g for the amorphous GLDA-$H_4$. The spray-dried, amorphous GLDA-$H_4$ showed a weight increase of more than ~8 wt %. The crystalline GLDA-$H_4$ had a weight increase of only 1 wt %

The comparison between the moisture uptake of amorphous GLDA-$H_4$ and the crystalline GLDA-$H_4$ as a function of time is shown in FIG. 3. This shows that the crystalline product has significantly reduced hygroscopic properties.

Comparative Example 5—Reworking EP0884381A1—Synthesis Example 1

The reactor was charged with 662.1 g Glutamic acid (ex Fluka), 738 g 40% NaOH (ex J. T. Baker) and 422 g demineralized water. Whilst stirring the reactor content was heated to 90° C. 233 g HCN, 855 g 30% formaldehyde (ex Fluka), and another 738 g 40% NaOH were dosed simultaneously within 2 hours. The resulting mixture was stirred at 105° C. for 2 hrs. The remaining cyanide was reduced to 47 ppm by the addition of 8 g 30% formaldehyde. The reaction mixture (3,490 grams) was cooled down to ambient temperature and was analyzed by titration on Fe—Total Sequestering Value being 20.1 wt % expressed as GLDA-$Na_4$.

This reaction mixture was analyzed by Capillary Zone Electrophorese (CZE) and the analytical data (Table 1) displayed that the sample still contained ~26 wt % of the precursor l-GLMA (i.e. linear glutamic acid monoacetic acid, also a cyclized version of this compound exists). The presence of such an amount of GLMA actually shows a very bad conversion to GLDA.

TABLE 1

Composition of reaction mixture

| Component | Wt % |
|---|---|
| IDA-$Na_2$ | 1.4 |
| HO—$CH_2$—COONa | 1 |
| GLMA | 26 |
| NTA-$Na_3$ | 3.5 |
| HCOONa | 0.34 |
| GLDA-$Na_4$ | 15.2 |

Preparation of the GLDA-$H_4$

To a 1 L-glass reactor provided with a 4-blade stirrer 543 g of the above reaction mixture were charged. Whilst stirring 333 g of 40% $H_2SO_4$ (ex J. T. Baker) were added. The pH of the reaction mixture became 1.8 (as is) at a temperature of 33° C. A sample of the aqueous liquid was analyzed by CZE (see Table 2). Because no crystallization was observed, the reaction mixture was seeded with a spatula tip of L-GLDA-$H_4$ crystals; however, these dissolved within 20 minutes. After the reactor content was cooled to ambient temperature additional seeds were added.

TABLE 2

Composition of aqueous solution that was allowed to crystallize

| Component | Wt % |
|---|---|
| IDA acid | 1.1 |
| Glycolic acid | 0.8 |
| GLMA acid | 19.5 |
| NTA-$H_3$ | 2.6 |
| Formic acid | 0.2 |
| $Na_2SO_4$ | 30.0 |
| GLDA-$H_4$ | 9.5 |
| % GLDA on total organic fraction | 28.1 |
| GLDA:inorganic material | ~1:3 |

After 11 days of stirring the reactor content was turned into white slurry. Microscopic determination showed large needle-shaped crystals. Besides the big crystals also very tiny, probably amorphous, particles were seen. The slurry was filtered applying a G2 glass filter, with 402 g wetcake being obtained. The Fe-TSV value was established to be about 4 wt % expressed as GLDA-H4. The mother liquor, being 343 grams, had a Fe-TSV of about 16% expressed as GLDA-H4. The wetcake was filtered off, dried, and analyzed by NMR (see Table 3 below) and XRD. Only 4 wt % was established to be organic material.

TABLE 3

Chemical composition of organics by NMR of the wetcake (~96% $Na_2SO_4$)

| Component | Wt % |
|---|---|
| GLDA-$H_4$ | 2.6 |
| GLMA acid | 0.6 |
| Glycolic acid | 0.5 |
| NTA-$H_3$ | 0.4 |
| Sum | ~4.0 |

XRD Determination

XRD and NMR analyses showed that the crystals in the sample were $Na_2SO_4$. When comparing the XRD diffractogram with a XRD diffractogram of crystalline L-GLDA-$H_4$ and D, L-GLDA-$H_4$ (as prepared in above Examples 2 and 3), it can be concluded that the procedure of Example 1 of EP-A-0884381 does not result in crystalline GLDA-$H_4$ and that the only crystals present in the sample are sulfate salt crystals.

The measured Fe-TSV value of the wetcake must be explained by a remaining small amount of moisture (mother liquor) attached to the salt crystals in the wetcake, as a calculation showed that the GLDA concentration in the reaction mixture and the amount of liquid present in the cake fit with the above explanation.

Reworking the procedure written in patent EP0884381A1—Synthesis Example 1 gave a reaction mixture with a relatively low amount of GLDA and a lot of the precursor GLMA, which indicates a low conversion, i.e. it was not possible to obtain comparable yields to those indicated in EP0884381A1. Most importantly, we did not observe any GLDA crystals in the product. This is primarily because the solution allowed to crystallize contains way too little GLDA. Additionally, the very high salt load and the presence of other organic material are also disturbing a crystallization of GLDA.

The invention claimed is:

1. Glutamic acid N,N-diacetic acid (GLDA) of the formula GLDA-$Y_mH_n$, wherein m is less than 0.5, n+m=4, Y is a monovalent cation that is not a proton, in the form of crystals.

2. GLDA-$Y_mH_n$ according to claim 1, wherein m is about 0.

3. GLDA-$Y_mH_n$ according to claim 1, wherein the GLDA-$Y_mH_n$ comprises L-GLDA-$Y_mH_n$ to D-GLDA-$Y_mH_n$ in a range of from 100:0 to 50:50 (L:D).

4. Process to prepare glutamic acid N,N-diacetic acid (GLDA) of the formula GLDA-$Y_mH_n$, wherein m is less than 0.5, n+m=4, Y is a monovalent cation that is not a proton, in the form of crystals, the process, comprising:
- a first step of providing an aqueous solution of GLDA or a salt thereof,
- a second step of ensuring that the pH of the aqueous solution is below 1.8, and
- a third step of allowing the aqueous solution to crystallize, wherein the aqueous solution that is allowed to crystallize contains at least 15 wt % of GLDA-$Y_mH_n$ on total solution.

5. Process according to claim 4, wherein the pH of the second step is in the range of between 1.0 and 1.7.

6. Process according to claim 4, wherein the second step includes a concentrating step that is carried out until the solution has a concentration of equal to or more than 15 wt % to up to or equal to 80 wt %, of GLDA-$Y_mH_n$ based on the weight of the aqueous solution.

7. Process according to claim 4, wherein the aqueous solution that is allowed to crystallize in the third step contains at least 75 wt % of GLDA-$Y_mH_n$ based on the total organic compounds.

8. Process according to claim 4, wherein the second step comprises a racemization step.

9. Process according to claim 4, wherein the third step comprises crystallization accomplished by one or more steps selected from the group consisting of allowing the solution to stand until the solution crystallizes, cooling, and seeding.

10. Process according to claim 4, wherein the third step comprises spraying the aqueous solution of the second step on seeding crystals.

11. Process according to claim 4, wherein the third step is performed at a temperature of equal to or below 30° C.

12. Process according to claim 4, wherein the process is a continuous process.

13. Detergent compositions containing glutamic acid N,N-diacetic acid (GLDA) of the formula GLDA-$Y_mH_n$, wherein m is less than 0.5, n+m=4, Y is a monovalent cation that is not a proton, in the form of crystals, and further comprising at least one component selected from the group consisting of cleaning additives, silicates, carbonates, bicarbonates, antiscaling additives, builders, protective colloids, chelating agents, surfactants, inorganic acids, organic acids, and corrosion inhibitors.

14. Pharmaceutical preparations containing glutamic acid N,N-diacetic acid (GLDA) of the formula GLDA-$Y_mH_n$, wherein m is less than 0.5, n+m=4, Y is a monovalent cation that is not a proton, in the form of crystals, and further comprising a pharmaceutically acceptable carrier.

15. Process according to claim 4 wherein the aqueous solution that is allowed to crystallize in the third step contains GLDA-$Y_mH_n$ in a weight ratio of GLDA-$Y_mH_n$:inorganic compounds of higher than 1:1.

16. Process according to claim 7 wherein the aqueous solution that is allowed to crystallize in the third step contains GLDA-$Y_mH_n$ in a weight ratio of GLDA-$Y_mH_n$:inorganic compounds of higher than 1:1.

* * * * *